United States Patent [19]

Knifton

[11] Patent Number: 4,827,048

[45] Date of Patent: May 2, 1989

[54] METHOD FOR ONE-STEP SYNTHESIS OF METHYL T-BUTYL ETHER

[75] Inventor: John F. Knifton, Austin, Tex.

[73] Assignee: Texaco Chemical Company, White Plains, N.Y.

[21] Appl. No.: 168,022

[22] Filed: Mar. 14, 1988

[51] Int. Cl.$^4$ ............................................... C07C 41/09
[52] U.S. Cl. ................................................... 568/698
[58] Field of Search ......................................... 568/698

[56] References Cited

U.S. PATENT DOCUMENTS

| | | | |
|---|---|---|---|
| 2,282,469 | 5/1942 | Frolich | 568/698 |
| 3,816,550 | 6/1974 | Young et al. | 568/694 |
| 4,058,576 | 11/1977 | Chang et al. | 568/698 |
| 4,612,301 | 9/1986 | Carrie et al. | 502/154 |

*Primary Examiner*—Howard T. Mars
*Attorney, Agent, or Firm*—Jack H. Park; Kenneth R. Priem; Cynthia L. Kendrick

[57] ABSTRACT

A method is disclosed for producing methyl tertiary butyl ether by reacting tertiary butyl alcohol and methanol in the presence of a catalyst comprising a heteropoly acid, such as 12-tungstophosphoric acid or 12-molybdophosphoric acid, on an inert support, such as titania, at an elevated temperature and moderate pressure.

13 Claims, No Drawings

METHOD FOR ONE-STEP SYNTHESIS OF METHYL T-BUTYL ETHER

CROSS-REFERENCE

This application is related to U.S. patent application Ser. Nos. 168,063, 168,064 and 167,948 filed of even date.

This invention concerns an improved process for preparing methyl tertiary butyl ether by the reaction of tertiary butanol and methanol in the presence of a catalyst comprising a heteropoly acid preferably on an inert support. The invention is particularly advantageous in that the reaction takes place in one-step, the of the catalyst exhibits excellent selectivity to desired ether product and high levels of tert-butanol conversion are achieved.

BACKGROUND OF THE INVENTION

It is known to those skilled in the art that ethers, including unsymmetrical ethers, may be prepared by reacting an alcohol with another alcohol to form the desired product. The reaction mixture, containing catalyst and/or condensing agent may be separated and further treated to permit attainment desired product. Such further treatment commonly includes one or more distillation operations.

Methyl tert-butyl ether is finding increasing use as a blending component in high octane gasoline as the current gasoline additives based on lead and manganese are phased out. Currently all commercial processes for the manufacture of methyl tert-butyl ether (MTBE) are based upon the liquid-phase reaction of isobutylene and methanol (eq. 1), catalyzed by a cationic ion-exchange resin (see, for example: hydrocarbon processing, Oct. 1984, p. 63; Oil and Gas J., Jan. 1, 1979, p. 76; Chem. Economics Handbook-SRI, Sept. 1986, p. 543-705:P). The cationic ion-exchange resins used in MTBE synthesis normally have the sulphonic acid functionality (see: J. Tejero, J. Mol. Catal., 42 (1987) 257; C. Subramamam et al., Can. J. Chem. Eng., 65 (1987) 613).

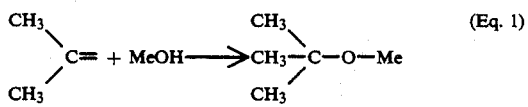

(Eq. 1)

With the expanding use of MTBE as an acceptable gasoline additive, however, a growing problem is the availability of raw materials. Historically, the critical raw material is isobutylene (Oil and Gas J., June 8, 1987, p. 55). It would be advantageous, therefore, to have a process to make MTBE that does not require isobutylene as a building block. Specifically, it would be advantageous to have an efficient process for making MTBE by reaction of methanol with tertiary butyl alcohol, since t-butanol is readily available commercially through isobutane oxidation.

In U.S. Pat. No. 4,144,138 (1979) to Rao et al., there is disclosed a method for recovering methyl tertiary butyl ether from etherification reaction effluent by azeotropic distillation to recover methanol-ether azeotrope overhead which is water-washed to give pure ether raffinate, the latter being azeotropically distilled to yield ether-methanol overhead which is recycled to water washing.

The preparation of methyl tert-butyl ether from methyl and tert-butyl alcohols i discussed in S. V. Rozhkov et al., Prevrashch Uglevodorodov, Kislotno-Osnovn. Geterogennykh Katal. Tezisy Dokl. Vses Konf., 1977, 150 (C. A. 92:58165y). Here the TBA and methanol undergo etherification over KU-2 strongly acidic sulfopolystyrene cation-exchangers under mild conditions. This reference contains data on basic parameters of such a process. It is also pointed out that, although a plant for etherification over cation exchangers does not present any problems, considerations include the fact that recycling large amounts of tert-butyl alcohol and methanol, as well as isobutylene, causes the scheme to be somewhat more expensive. Also, the progress of the reaction over cation exchangers is usually complicated by various adsorption and diffusion factors, by swelling phenomena, and by the variable distribution of the components between the solution and ion-exchanger phase. Furthermore, said acidic cation-exchangers with an organic (polystyrene or polymethacrylate) backbone generally have a very limited stability range with regard to operating temperatures, with temperatures above 120° C. normally leading to irreversible destruction of the resin and loss of catalytic activity.

It would be a substantial advance in the art if methyl tertiary butyl ether could be selectively synthesized from tertiary butyl alcohol and methanol in one step using an inorganic, heterogeneous catalyst that was thermally stable to temperatures above 120° C., preferably to temperatures up to 200° C.

SUMMARY OF THE INVENTION

In accordance with certain of its aspects, the novel method of this invention for preparing methyl tert-butyl ether from tertiary butyl alcohol (t-butanol) and methanol in one-step comprises reacting tertiary butyl alcohol and methanol in the presence of a catalyst comprising a heteropoly acid, preferably on an inert, high surface area support at an elevated temperature and moderate pressure.

DESCRIPTION OF THE INVENTION

Preparation of the product of this invention may be carried out typically by reacting tertiary butyl alcohol and methanol in the presence of an etherification catalyst deposited an inert support. The etherification is carried out in one step and the catalyst preferably comprises a heteropoly acid on a titania-containing compound.

The reaction can be represented by the following:

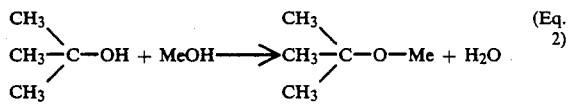

(Eq. 2)

Generally the methanol and t-butanol coreactants may be mixed in any proportion in order to generate the desired methyl t-butyl ether, but preferably the molar ratio of methanol to t-butanol in the feed mixture should be between 10:1 and 1:10, if the yield of desired MTBE is to be maximized. In order to achieve maximum selectivity to MTBE, and optimum conversion per pass, an excess of melhanol in the liquid feed is desirable. The most preferred methanol-to-tertiary butanol molar ratio is from 1:1 to 5:1.

The same process may also be applied to the preparation of other alkyl tertiary alkyl ethers. For example, said process may be applied to the reaction of a $C_1$–$C_6$ primary alcohol such as methanol, ethanol, n-propanol and n-hexanol with a $C_4$–$C_{10}$ tertiary alcohol such as, for example, tertiary butanol and tertiary amyl alcohol. Reaction of methanol with tertiary amyl alcohol (2-methyl-2-butanol) would then yield methyl tertiary amyl ether (TAME). Alternatively a mixture of alcohols, e.g., a mixture of $C_1$–$C_5$ alcohols, could be reacted to give a mixture of alkyl tert-alkyl ethers.

The heteropoly acids that are catalysts in the subject reaction comprise a class of acids formed by the condensation of two or more inorganic oxyacids. For example, phosphate and tungstate ions, when reacted in an acidic medium, are condensed to form 12-tungstophosphoric acid, a typical heteropoly acid (HPA) according to Equation 3:

$$PO_4^{3-} + 12WO_4^{2-} + 27H^+ \rightarrow H_3PW_{12}O_{40} + 12H_2O$$
(Eq. 3)

A wide variety of elements ranging from Group I to Group VIII can become the central atom of the HPA anion, or the heteroatom as it is called (P in the case of Eq. 3). The nature of the heteroatom is a governing factor which determines both the condensation structure and the physical properties of the HPA.

Atoms coordinated to the heteroatom via oxygens are called polyatoms (W in the case of Equation 3) and in most cases are any one of such limited species as molybdenum, tungsten, niobium and vanadium. In the case of molybdenum (Mo) as the polyatom, the nature of the heteroatoms, condensation ratios and chemical formulae of the corresponding HPA anions are summarized in Table I.

Anions containing the so-called Keggin structure have a condensation ratio of 1:12 and are the most typical of all HPA anions. Heteropoly acids with the Keggin structure, and their homologues, are generally the most readily available HPA's and the ones most commonly used in catalysis. The synthesis of these HPA's is well documented in the literature (see for example U.S. Pat. No. 3,947,332 (1976).

icic acid, $H_4SiMo_{12}O_{40}$ and tungstosilicic acid. Said acids are generally used as their hydrates; they may be employed by themselves, partially or completely dissolved in the methanol tert-butanol feed, or they may be employed as heterogeneous catalysts bonded to a suitable support.

The support should preferably comprise an inert compound. Compounds which may be employed are those containing elements of Group III and IV of the periodic table. Suitable compounds include the oxides of Al, Si, Ti and Zr, e.g. alumina, silica (silicon dioxide), titania (titanium dioxide) and zirconia, as well as combinations thereof. Also suitable are carbon, ion-exchange resins and carbon-containing supports. The use of alumina (aluminum oxide, $Al_2O_3$) is also demonstrated in Example 7, silica is illustrated in Examples 6 and 9. A mixed $SiO_2$ and $Al_2O_3$ support is demonstrated. Good results were observed using $TiO_2$ as the support.

The inert support may be in the form of powders, pellets, spheres, shapes and extrudates. The examples described herein demonstrate the advantages of using pellets and extrudates. A extrudate which works well is HSA titania carrier extrudate from Norton Company, ⅛″ extrudates with a surface area of 51 m²/g. Another titania extrudate, used in Example 2 is from Norton Company, ⅛″ extrudate with a surface area of 60 m²/g.

As will be demonstrated by the examples, the supports are preferably of high purity and high surface area. It has been found in the process of this invention that greater conversion of tertiary butanol and methanol is achieved where the surface area of the support is generally >10 m²/g.

The reaction may be carried out in either a stirred slurry reactor or in a fixed bed continuous flow reactor. The catalyst concentration should be sufficient to provide the desired catalytic effect.

The weight percent of heteropoly acid to Group III/Group IV support should be such that the concentration of the polyatom (Mo, W, Nb or V) in the formulated catalyst is in the range of 0.1 wt % to 30 wt %. Although concentrations outside this range may also be employed. Where the heteropoly acid is, for example,

TABLE 1

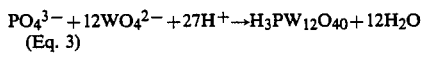

| Typical heteropolymolybdate anions | | |
|---|---|---|
| CONDENSATION RATIOS | HETERO ATOMS (X) | CHEMICAL FORMULAS |
| 1:12 Keggin structure | $P^{5+}$, $As^{5+}$, $Si^{4+}$, $Ge^{4+}$ | $[X^{n+}Mo_{12}O_{40}]^{-(8-n)}$ |
| Silverton structure | $Ce^{4+}$, $Th^{4+}$ | $[X^{4+}Mo_{12}O_{42}]^{8-}$ |
| 1:11 Keggin structure (decomposition) | $P^{5+}$, $As^{5+}$, $Ge^{4+}$, $Si^{4+}$ | $[X^{n+}Mo_{11}O_{39}]^{-(12-n)}$ |
| 2:18 Dawson structure | $P^{5+}$, $As^{5+}$ | $[X_2^{5+}Mo_{18}O_{62}]^{6-}$ |
| 1:9 Waugh structure | $Mn^{4+}$, $Ni^{4+}$ | $[X^{4+}Mo_9O_{32}]^{6-}$ |
| 1:6 Anderson structure | | |
| (A type) | $Te^{6+}$, $I^{7+}$ | $[X^{n+}Mo_6O_{24}]^{-(12-n)}$ |
| (B type) | $Co^{3+}$, $Al^{3+}$, $Cr^{3+}$ | $[X^{n+}Mo_6O_{24}H_6]^{-(6-n)}$ |
| 4:12 | $As^{5+}$ | $[H_4As_4Mo_{12}O_{52}]^{4-}$ |
| 2:5 | $P^{5+}$ | $[P_2Mo_5O_{23}]^{6-}$ |

In the case of etherification to generate MTBE, suitable heterpoly acid catalysts may contain polyatoms selected from the group molybdenum, tungsten, niobium and vanadium, while the heteroatoms may be phosphorus, silicon, germanium, and arsenic. Preferably the heteroatoms are phosphorus or silicon. These heteropoly acids would likely have the Keggin structure, $H_{8-n}[XM_{12}O_{40}]$, were X=P or Si, M=Mo or W and n is an integer, 4 or 5.

The preferred heteropoly acids for the practice of this invention include 12-molybdophosphoric acid $H_3PMo_{12}O_{40}$, 12-tungstophosphoric acid, molybdosil- 12-molybdophosphoric acid, supported on titania, a suitable quantity of molybdenum is 1–10 wt %. In the preparation of a tungstophosphoric acid-on-titania catalyst, on the other hand, the tungsten content may be 1–30 wt %.

Etherification can generally be conducted at temperatures from 20° to 200° C.; the preferred range is 100° to 180° C. The total operating pressure may be from 0 to 1000 psig, or higher. The preferred pressure range is 50 to 500 psig.

Typically, MTBE is generated continuously in up to 40+ wt % concentration in the crude liquid product at total liquid hourly space velocities (LHSV) of up to eight and relatively mild conditions, where:

$$LHSV = \frac{\text{Volume Of Total Liquid Feed Run Through The Reactor Per Hour}}{\text{Volume of Catalyst In Reactor}}$$

Typical preparation of the catalyst involves impregnating the heteropoly acid onto the inert support using the incipient wetness technique as in the following manner:

(1) In the case where 12-molybdophosphoric acid is impregnated on titania, a solution of 12-molybdophosphoric acid (10.0 g) in water (50 ml) was added, with stirring, to 125 cc of HSA titania carrier extrudate (from Norton Company, ⅛" extrudates, surface area 51 m²/g). The liquid was absorbed into the extrudates, with stirring, for 1-2 hours. The mixture was then rotary evaporated to remove excess liquid and calcined at 100°-150° C. in vacuo.

Weight of recovered, yellow-color, extrudates: 116 g (Sample #5972-57R₂)
Analyses showed the presence of:
Mo=2.2% P=0.08%

(2) Where 12-tungstophosphoric acid is used on titania a solution of 2-tungstophosphoric acid (40.0g) in water (150 ml) was added, with stirring to 125 cc of HSA titania carrier extrudates (from Norton Company, ⅛" extrudates, surface area 60 m²/g). The liquid was absorbed into the extrudates, with stirring, for 1-2 hours. The mixture was then rotary evaporated to remove excess liquid and calcined at 150°-350° C. under slow nitrogen flow conditions.

Weight of recovered, grey-colored, extrudates: 151 g (Sample #5972-83R)
Analyses showed the presence of:
W=17.0%
P=0.33%

The examples which follow illustrate the one-step synthesis of MTBE from TBA and MeOH (Eq. 2) using heteropoly acids, particularly 12-molybdophosphoric acid and 12-tungstophosphoric acid on high surface area titania. The examples are only intended as a means of illustration and it is understood the invention is not meant to be limited thereby. Conversion of t-butanol (TBA, wt %) are estimated in the following examples using the equation:

$$\frac{(\text{Wt \% Conc. of TBA in Feed} - \text{Wt \% Conc. of TBA in Product})}{\text{Wt \% Conc of TBA in Feed}} \times 100$$

Yields of methyl t-butyl ether (MTBE, mole %) are estimated from:

$$\frac{\text{Moles of MTBE in Product Liquid}}{\text{moles of TBA converted}} \times 100$$

EXAMPLE 1

This example illustrates the synthesis of methyl t-butyl ether from t-butanol and methanol using a 12-molybdophosphoric acid-on-titania catalyst.

The synthesis was conducted in a tubular reactor (0.563" id; 12" long), constructed of 316 stainless steel, operated upflow and mounted in a furnace, controllable to ±1.0° C. and fitted with pumps allowing flow control to <±1 cc/hr. The reactor was also fitted with a pressure regulating device and equipment for monitoring temperature, pressure and flow rate.

The reactor was charged at the beginning of the experiment with 25 cc of 12-molybdophosphoric acid-on-titania extrudates (prepared as described SUPRA). A screen of glass beads was placed at the top and bottom of the reactor to ensure the extrudates would remain in the middle portion. The catalyst bed was first conditioned overnight by washing with methanol/t-butanol (2:1 mix) at 100° C., 300 psi back pressure and a liquid flow rate of 25 cc/hr. The same solution of methanol (1281.6 g, 40.0 mole) plus t-butanol (1482.4 g 20.0 mole) was then pumped through the catalyst bed at 25 cc/hr, while the reactor was held at 100° C., at a total pressure of 300 psi. Samples of product were taken periodically, either by trapping in a dry ice cooled container, or by collecting on-stream (on line) in a 316 ss bomb. Typical analyses data for samples taken under these conditions are summarized in Table II. Catalyst performance at other operating temperatures and liquid flow rates was also measured, after reaching equilibrium conditions overnight. Summary data for these runs are also given in Table II.

In this run the 12-molybdophosphoric acid on titania catalyst gave MTBE in ca. 36% concentration in the crude liquid product when run at LHSV of 1 (eq. sample #18) and ca. 34% concentration when run at LHSV of 4 (eg. #23). The operating conditions in both cases (150° C., 300 psig) are moderate. This catalyst was screened over the temperature range 100°-150° C. At 150° C., LHSV=4, Sample #21 shows:

Estimated TBA conversion per pass=73%
MTBE yield (basis TBA converted)=77 mole %

TABLE II

| Catalyst | Feed Sample | Flow Rate (cc/hr) | Pressure (psig) | Temp. (°C.) | Sample | PRODUCT COMPOSITION (WT %)[c] | | | | | |
|---|---|---|---|---|---|---|---|---|---|---|---|
| | | | | | | MTBE | i-C₄ | MeOH | tBA | H₂O | |
| H₃PO₄.12MoO₃/TiO₂[a] | F | | | | | | | | 47.5 | 52.4 | |
| | | 25 | 300 | 100 | #1 | 17.0 | 1.8 | 40.7 | 35.7 | 4.7 | |
| | | | | | #5 | 18.0 | 1.5 | 40.7 | 34.9 | 4.9 | |
| | | | | | #6 | 23.2 | 2.2 | 38.5 | 30.2 | 6.0 | [b] |
| " | | 25 | 300 | 120 | #7 | 35.6 | 5.0 | 32.5 | 16.1 | 10.6 | |
| | | | | | #10 | 35.6 | 3.1 | 33.3 | 16.9 | 11.1 | |
| | | | | | #12 | 31.8 | 3.1 | 34.9 | 21.6 | 8.5 | [b] |
| " | | 25 | 300 | 150 | #13 | 36.1 | 9.5 | 34.8 | 11.1 | 11.5 | |
| | | | | | #15 | 37.0 | 7.3 | 32.5 | 11.1 | 11.9 | |
| | | | | | #18 | 36.2 | 7.6 | 32.1 | 11.7 | 11.6 | [b] |

TABLE II-continued

| Catalyst | Feed Sample | Flow Rate (cc/hr) | Pressure (psig) | Temp. (°C.) | Sample | MTBE | i-C$_4$ | MeOH | tBA | H$_2$O | |
|---|---|---|---|---|---|---|---|---|---|---|---|
| " | | 100 | 300 | 150 | #21 | 34.8 | 6.5 | 33.5 | 14.4 | 10.7 | |
| | | | | | #22 | 34.0 | 6.8 | 33.7 | 14.2 | 11.3 | |
| | | | | | #23 | 34.3 | 6.8 | 33.7 | 14.1 | 11.2 | (b) |

[a] 12-Molybdophosphoric acid-on-titania, sample 5972-57R
[b] On-Line sample
[c] Methyl t-butyl ether (MTBE), isobutylene (i-C$_4$), methanol (MeOH) and t-butanol (tBA)

EXAMPLES 2 AND 3

These examples illustrate the synthesis of methyl t-butyl ether from t-butanol and methanol using a 12-tungstophosphoric acid-on-titania catalyst.

In Example 3, Table III, MTBE is generated over several days at LHSV's up to eight. In the case of Sample #13, running at a feed rate of 200 cc/hr. (LHSV=8), at 150° C., the crude liquid product contains ca. 26% MTBE.

TABLE III

| Catalyst | Feed Sample | Flow Rate (cc/hr) | Pressure (psig) | Temp. (°C.) | Sample | MTBE | i-C$_4$ | MeOH | tBA | H$_2$O | |
|---|---|---|---|---|---|---|---|---|---|---|---|
| H$_3$PO$_4$.12WO$_3$/TiO$_2$[a] | F | | | | | | | 47.1 | 52.7 | | |
| | | 25 | 300 | 100 | #1 | 27.6 | 1.7 | 37.0 | 25.9 | 7.7 | |
| | | | | | #4 | 27.5 | 1.3 | 37.2 | 26.1 | 7.8 | |
| | | | | | #6 | 27.6 | 1.4 | 37.0 | 26.1 | 7.7 | |
| " | F-1 | | | | | | | 47.3 | 52.6 | | |
| | | 25 | 300 | 150 | #8 | 37.0 | 4.2 | 33.1 | 11.9 | 13.5 | |
| | | | | | #11 | 37.6 | 5.7 | 32.3 | 11.6 | 12.7 | |
| | | | | | #12 | 36.9 | 6.7 | 32.5 | 12.2 | 11.6 | (b) |
| " | | 25 | 300 | 180 | #13 | 24.0 | 8.4 | 43.4 | 5.8 | 18.2 | |
| | | | | | #17 | 25.4 | 3.7 | 45.9 | 6.1 | 18.8 | |
| | | | | | #18 | 22.3 | 18.8 | 37.2 | 5.5 | 14.5 | (b), (c) |

[a] 12 Tungstophosphoric Acid-On-Titiania, Sample 5972-83R
[b] On-Line Sample
[c] Same also contained 1.8% Me$_2$O

TABLE IV

| Catalyst | Feed Sample | Flow Rate (cc/hr) | Pressure (psig) | Temp. (°C.) | Sample | MTBE | i-C$_4$ | MeOH | tBA | H$_2$O | |
|---|---|---|---|---|---|---|---|---|---|---|---|
| H$_3$PO$_4$.12WO$_3$/TiO$_2$[a] | F | | | | | | | 47.4 | 52.4 | | |
| | | 25 | 300 | 150 | #1 | 36.9 | 5.1 | 32.8 | 12.1 | 12.7 | |
| | | | | | #3[b] | 36.9 | 5.7 | 33.0 | 12.1 | 12.0 | |
| | | | | | #4[c] | 37.1 | 8.8 | 31.3 | 11.5 | 11.2 | |
| " | | 100 | 300 | 150 | #8 | 33.2 | 6.4 | 33.9 | 15.4 | 11.0 | |
| | | | | | #10 | 33.0 | 5.7 | 34.3 | 15.7 | 11.2 | |
| | | | | | #11 | 33.3 | 6.6 | 34.1 | 16.1 | 10.0 | (d) |
| " | | 200 | 300 | 150 | #13[e] | 26.1 | 4.0 | 37.5 | 23.4 | 8.8 | |
| | | | | | #17 | 25.4 | 4.7 | 37.5 | 24.0 | 8.3 | |
| | | | | | #19 | 25.5 | 5.3 | 37.4 | 24.0 | 7.8 | (d) |

[a] 12-Tungstophsphoric Acid-On-Titania, Sample 5972-83R
[b] After 4 days running, composite sample
[c] After 4 days running, composite sample
[d] On-line sample
[e] After 1 day running, composite sample The syntheses are conducted using the equipment, feed, and procedures of Example 1. The reactor is charged with 25 cc of 12-tungstophosphoric acid-on-titania, containing 17.0% W, prepared as described SUPRA. Results are summarzied in Tables III and IV.

In Example 2, MTBE is generated in ca. 37% concentration in the crude liquid product when run at LHSV of 1 and moderate conditions (e.g. 150° C., 300 psig, Sample #12, Table III).

The catalyst was screened over a range of temperatures, from 100° to 180° C. At 150° C., Sample #12 shows:
  Estimated TBA conversion per pass=77%
  MTBE yield (basis TBA converted)=77 mole %

EXAMPLE 4

This example illustrates the synthesis of methyl t-butyl ether using a second sample of the same 12-molybdophosphoric acid-on-titania catalyst of Example 1, but at higher liquid feed rate (e.g. 200 cc/hr., LHSV=8) and higher operating temperatures (to 160° C.). Data are summarized in Table V.

At a t-butanol/methanol (1:2 molar ratio) feed rate of 200 cc/hr (LHSV=8), and 160° C. operating temperature, sample #25 shows a MTBE concentration in the crude liquid product of ca. 35 wt %. In this case:
  Estimated TBA Conversion Per Pass=70%
  MTBE Yield (Basis TBA Converted)=80 mole %

TABLE V

| Catalyst | Feed Sample | Flow Rate (cc/hr) | Pressure (psig) | Temp. (°C.) | Sample | MTBE | i-C$_4$ | MeOH | tBA | H$_2$O |
|---|---|---|---|---|---|---|---|---|---|---|
| H$_3$PO$_4$.12MoO$_3$/TiO$_2$[a] | F | | | | | | | 47.7 | 52.1 | |
| | | 100 | 300 | 150 | #1 | 33.7 | 5.1 | 34.4 | 15.5 | 11.2 |

TABLE V-continued

| Catalyst | Feed Sample | Flow Rate (cc/hr) | Pressure (psig) | Temp. (°C.) | Sample | PRODUCT COMPOSITION (WT %) | | | | | |
|---|---|---|---|---|---|---|---|---|---|---|---|
| | | | | | | MTBE | i-C$_4$ | MeOH | tBA | H$_2$O | |
| | | | | | #6 | 33.4 | 5.7 | 34.2 | 16.0 | 10.6 | |
| | | | | | #7 | 35.5 | 6.1 | 33.6 | 16.7 | 8.1 | (b) |
| " | | 200 | 300 | 150 | #9 | 31.5 | 4.8 | 35.1 | 20.7 | 7.8 | |
| | | | | | #12 | 31.8 | 5.2 | 34.9 | 20.1 | 7.9 | |
| | | | | | #13 | 32.0 | 5.5 | 35.1 | 20.2 | 7.2 | (b) |
| " | | 200 | 300 | 140 | #17 | 27.8 | 3.8 | 36.5 | 25.2 | 6.6 | |
| | | | | | #18 | 28.2 | 4.0 | 36.3 | 24.9 | 6.6 | |
| | | | | | #19 | 28.4 | 4.4 | 36.3 | 24.8 | 6.1 | (b) |
| " | | 200 | 300 | 160 | #20 | 34.7 | 8.1 | 33.3 | 15.2 | 8.6 | |
| | | | | | #24 | 35.1 | 7.4 | 33.6 | 15.2 | 8.6 | |
| | | | | | #25 | 34.9 | 7.1 | 34.0 | 15.4 | 8.5 | (b) |

(a)12-Molybdophosphoric Acid-On-Titania, Sample 5972-57R
(b)On-Line Sample

EXAMPLE 5

This example illustrates the synthesis of methyl t-butyl ether using a second 12-tungstophosphoric acid-on-titania catalyst. This 12-tungstophosphoric acid-on-titania catalyst is prepared by a procedure similar to the one used to prepare the catalysts of Example 2, but contains 6.0 wt % W. The support is titania carrier extrudate from Norton Company, ⅛" extrudates with a surface area of 120 m$^2$/g.

At a t-butanol/methanol (1:2 molar ratio) feed rate of 25 cc/hr (LHSV:1) and 160° C. operating temperature, Sample #18 shows a MTBE concentration in the crude liquid product of ca. 39 wt %.

Data for this run are summarized in Table VI.

Tungsten loadings are in the range 5-20 wt %, results are given in Tables VII-X.

Of Note:
(a) In Table VII, with the tungstophosphoric acid-on-silica catalyst, at 150° C., 25 cc/hr. feed rate, MTBE is generated in ca. 46 wt % concentration (see Sample #17). Here:
    Estimated TBA Conversion is 81%
    MTBE yield (basis TBA Converted)=89 mole %
(b) In Table VIII, with the tungstophosphoric acid-on-alumina catalyst at 150° C., 25 cc/hr. feed rate, MTBE is generated in ca. 40 wt % concentration (see Sample #15). Here:
    Estimated TBA Conversion is 76%
    MTBE yield (basis TBA Converted)=81 mole %

TABLE VI

| Catalyst | Feed Sample | Flow Rate (cc/hr) | Pressure (psig) | Temp. (°C.) | Sample | PRODUCT COMPOSITION (WT %) | | | | | |
|---|---|---|---|---|---|---|---|---|---|---|---|
| | | | | | | MTBE | i-C$_4$ | MeOH | tBA | H$_2$O | |
| | F | | | | | | | 46.2 | 53.8 | | |
| H$_3$PO$_4$.12WO$_3$/TiO$_2$(a) | | 25 | 300 | 120 | #3 | 23.4 | 2.9 | 37.8 | 30.3 | 5.2 | |
| | | | | | #4 | 24.6 | 3.3 | 37.6 | 29.5 | 5.1 | |
| | | | | | #5 | 23.0 | 2.7 | 38.5 | 31.0 | 4.7 | (b) |
| " | | 25 | 300 | 140 | #6 | 34.9 | 6.0 | 33.3 | 17.7 | 8.2 | |
| | | | | | #10 | 32.4 | 5.0 | 34.6 | 20.8 | 7.2 | (b) |
| " | | 25 | 300 | 150 | #14 | 37.0 | 5.4 | 33.2 | 15.8 | 8.5 | |
| | | | | | #15 | 36.8 | 7.0 | 32.4 | 15.2 | 8.6 | |
| | | | | | #16 | 34.6 | 5.4 | 34.5 | 17.5 | 8.0 | (b) |
| " | | 25 | 300 | 160 | #18 | 38.9 | 8.5 | 31.6 | 12.3 | 8.6 | |
| | | | | | #20 | 38.4 | 8.8 | 31.6 | 12.1 | 9.1 | |
| | | | | | #21 | 36.0 | 8.7 | 33.4 | 12.8 | 9.2 | (b) |

(a)12-Tungstophosphoric Acid-On-Titania, Sample 5972-81R, W-6.0%
(b)On-Line Sample

EXAMPLES 6-9

These examples illustrate the synthesis of methyl t-butyl ether using a series of 12-tungstophosphoric acid-supported catalysts. These catalysts comprise 12-tungostophosphoric acid supported on silica (Table VII), acidic alumina (Table VIII) silica-alumina (Table IX) and silica gel (Table X). Each of these catalysts was prepared by an incipient wetness procedure similar to the one used to preparing the catalyst of Example 2.

(c) In Table IX, a tungstophosphoric acid-on-silica-alumina is shown to generate MTBE over the temperature range 120°-160° C.
(d) In Table X are illustrated two evaluations of a 12-tungstophosphoric acid-on-silica gel catalyst, made at different operating temperatures (120°-150° C.) and feed rates (25-100 cc/hr). The silica gel support in this case has a surface ara of 600 m$^2$/g, and a pore volume of 1 cc/g.

TABLE VII

| Catalyst | Feed Sample | Flow Rate (cc/hr) | Pressure (psig) | Temp. (°C.) | Sample | PRODUCT COMPOSITION (WT %) | | | | | |
|---|---|---|---|---|---|---|---|---|---|---|---|
| | | | | | | MTBE | i-C$_4$ | MeOH | tBA | H$_2$O | |
| | F | | | | | | | 46.4 | 53.5 | | |
| | | 25 | 300 | 120 | #2 | 25.5 | 2.8 | 37.5 | 28.1 | 6.0 | |
| H$_3$PO$_4$.12WO$_3$/SiO$_2$(a) | | | | | #3 | 24.6 | 2.5 | 39.8 | 31.1 | 1.9 | |
| | | | | | #6 | 16.7 | 4.3 | 40.6 | 34.4 | 4.0 | (b) |
| " | | 25 | 300 | 140 | #8 | 35.9 | 5.2 | 33.4 | 17.1 | 8.3 | |
| | | | | | #9 | 35.2 | 5.2 | 33.8 | 17.2 | 8.5 | |
| | | | | | #12 | 34.4 | 6.9 | 34.1 | 16.5 | 8.2 | (b) |
| " | | 25 | 300 | 150 | #13 | 41.9 | 12.1 | 27.9 | 10.5 | 7.6 | |
| | | | | | #17 | 45.9 | 8.7 | 27.9 | 10.0 | 7.5 | |

TABLE VII-continued

| Catalyst | Feed Sample | Flow Rate (cc/hr) | Pressure (psig) | Temp. (°C.) | Sample | PRODUCT COMPOSITION (WT %) | | | | | |
|---|---|---|---|---|---|---|---|---|---|---|---|
| | | | | | | MTBE | i-$C_4$ | MeOH | tBA | $H_2O$ | |
| | | | | | #18 | 38.3 | 7.6 | 32.6 | 12.4 | 9.2 | (b) |
| " | | 25 | 300 | 160 | #19 | 37.0 | 4.8 | 35.1 | 11.9 | 11.1 | |
| | | | | | #22 | 41.4 | 7.4 | 30.6 | 9.9 | 10.7 | |
| | | | | | #24 | 37.7 | 7.9 | 33.2 | 11.2 | 10.0 | (b) |
| " | | 100 | 300 | 150 | #26 | 15.9 | 3.9 | 40.7 | 35.3 | 4.1 | |
| | | | | | #29 | 14.8 | 3.6 | 41.3 | 36.6 | 3.7 | |
| | | | | | #30 | 13.8 | 3.5 | 41.7 | 37.8 | 3.0 | (b) |
| " | | 200 | 300 | 150 | #32 | 4.4 | 1.1 | 45.0 | 48.3 | 1.2 | |
| | | | | | #34 | 4.1 | 1.0 | 45.2 | 48.7 | 0.9 | |
| | | | | | #36 | 4.2 | 1.1 | 45.2 | 49.1 | 0.4 | (b) |

(a) 12-Tungstophosphoric Acid-On-Silica, Sample 5972-99
(b) On-Line Sample

TABLE VIII

| Catalyst | Feed Sample | Flow Rate (cc/hr) | Pressure (psig) | Temp. (°C.) | Sample | PRODUCT COMPOSITION (WT %) | | | | | |
|---|---|---|---|---|---|---|---|---|---|---|---|
| | | | | | | MTBE | i-$C_4$ | MeOH | tBA | $H_2O$ | |
| | F | | | | | | | 45.9 | 54.0 | | |
| $H_3PO_4.12WO_3/Al_2O_3$(a) | | 25 | 300 | 120 | #3 | 28.7 | 2.8 | 35.8 | 26.4 | 6.3 | |
| | | | | | #4 | 28.5 | 2.8 | 35.9 | 26.5 | 6.4 | |
| | | | | | #6 | 27.8 | 3.5 | 36.4 | 26.4 | 5.9 | (b) |
| " | | 25 | 300 | 140 | #10 | 41.0 | 6.1 | 30.8 | 14.1 | 8.0 | |
| | | | | | #11 | 40.8 | 5.8 | 31.0 | 14.2 | 8.1 | |
| | | | | | #12 | 44.5 | 5.8 | 27.3 | 19.4 | 3.0 | (b) |
| " | | 25 | 300 | 150 | #13 | 42.4 | 11.7 | 27.7 | 10.7 | 7.4 | |
| | | | | | #15 | 39.7 | 6.2 | 31.8 | 12.8 | 9.4 | |
| | | | | | #18 | 37.2 | 6.7 | 33.0 | 13.8 | 9.2 | (b) |
| " | | 25 | 300 | 160 | #21 | 40.3 | 13.1 | 28.7 | 9.4 | 8.2 | |
| | | | | | #22 | 39.7 | 6.8 | 32.6 | 11.1 | 9.7 | |
| | | | | | #24 | 35.7 | 7.6 | 33.5 | 13.7 | 9.5 | (b) |
| " | | 100 | 300 | 150 | #26 | 30.7 | 7.2 | 34.4 | 20.4 | 7.3 | |
| | | | | | #28 | 30.1 | 5.9 | 35.4 | 21.0 | 7.7 | |
| | | | | | #29 | 30.0 | 5.7 | 35.5 | 21.3 | 7.4 | (b) |
| " | | 200 | 300 | 150 | #30 | 22.4 | 4.6 | 37.8 | 29.3 | 5.9 | |
| | | | | | #34 | 22.7 | 4.6 | 38.1 | 28.8 | 5.8 | |
| | | | | | #35 | 22.6 | 5.1 | 38.0 | 28.9 | 5.5 | (b) |

(a) 12-Tungstophosphoric Acid-On-Super Acid Alumina, Sample 5972-100
(b) On-Line Sample

TABLE IX

| Catalyst | Feed Sample | Flow Rate (cc/hr) | Pressure (psig) | Temp. (°C.) | Sample | PRODUCT COMPOSITION (WT %) | | | | | |
|---|---|---|---|---|---|---|---|---|---|---|---|
| | | | | | | MTBE | i-$C_4$ | MeOH | tBA | $H_2O$ | |
| | F | | | | | | | 46.2 | 53.8 | | |
| $H_3PO_4.12WO_3/SiO_2-Al_2O_3$(a) | | 25 | 300 | 120 | #1 | 10.4 | 2.9 | 41.7 | 41.8 | 3.2 | |
| | | | | | #5 | 10.4 | 1.8 | 42.6 | 42.5 | 2.8 | |
| | | | | | #6 | 11.5 | 2.1 | 42.6 | 41.3 | 2.5 | (b) |
| " | | 25 | 300 | 140 | #7 | 24.7 | 8.1 | 35.6 | 26.4 | 5.2 | |
| | | | | | #10 | 24.3 | 4.1 | 37.3 | 28.1 | 6.1 | |
| | | | | | #12 | 22.8 | 4.0 | 38.4 | 29.2 | 5.6 | (b) |
| " | | 25 | 300 | 150 | #13 | 30.0 | 5.1 | 35.5 | 22.4 | 7.2 | |
| | | | | | #17 | 29.5 | 5.8 | 35.4 | 21.7 | 7.6 | |
| | | | | | #18 | 28.7 | 5.5 | 36.3 | 22.5 | 7.0 | (b) |
| " | | 25 | 300 | 160 | #25 | 34.9 | 9.2 | 32.5 | 15.4 | 8.0 | |
| | | | | | #28 | 33.0 | 5.1 | 35.0 | 17.3 | 9.6 | |
| | | | | | #29 | 32.1 | 6.9 | 35.2 | 17.4 | 8.4 | (b) |
| " | | 100 | 300 | 150 | #19 | 17.3 | 4.4 | 40.1 | 33.8 | 4.4 | |
| | | | | | #20 | 16.1 | 3.9 | 40.5 | 35.2 | 4.3 | |
| | | | | | #23 | 15.5 | 3.6 | 41.0 | 36.3 | 3.6 | (b) |

(a) 12-Tungstophosphoric Acid-On-Silica-Alumina, Sample 6298-2
(b) On-Line-Sample

TABLE X

| Catalyst | Feed Sample | Flow Rate (cc/hr) | Pressure (psig) | Temp. (°C.) | Sample | PRODUCT COMPOSITION (WT %) | | | | | |
|---|---|---|---|---|---|---|---|---|---|---|---|
| | | | | | | MTBE | i-$C_4$ | MeOH | tBA | $H_2O$ | |
| | F | | | | | | | 46.2 | 53.5 | | |
| $H_3PO_4.12WO_3/SiO_2$(a) | | 25 | 300 | 120 | #4 | 25.3 | 3.4 | 36.8 | 28.6 | 5.9 | |
| | | | | | #5 | 22.6 | 2.8 | 37.7 | 29.8 | 7.1 | |
| | | | | | #6 | 22.3 | 2.6 | 39.0 | 31.2 | 4.9 | (b) |
| " | | 25 | 300 | 140 | #7 | 30.5 | 8.2 | 33.6 | 21.1 | 6.6 | |
| | | | | | #8 | 29.5 | 4.6 | 33.7 | 23.4 | 6.9 | |
| | | | | | #12 | 24.3 | 4.6 | 37.9 | 27.3 | 5.8 | (b) |
| " | | 25 | 300 | 150 | #13 | 24.1 | 7.1 | 36.6 | 25.5 | 6.8 | |
| | | | | | #14 | 26.7 | 5.4 | 36.5 | 25.4 | 6.0 | |

TABLE X-continued

| Catalyst | Feed Sample | Flow Rate (cc/hr) | Pressure (psig) | Temp. (°C.) | Sample | PRODUCT COMPOSITION (WT %) | | | | | |
|---|---|---|---|---|---|---|---|---|---|---|---|
| | | | | | | MTBE | i-C$_4$ | MeOH | tBA | H$_2$O | |
| | | | | | #18 | 21.0 | 4.4 | 39.3 | 30.1 | 5.2 | (b) |
| | | | | | | | | 46.5 | 53.5 | | |
| H$_3$PO$_4$.12WO$_3$/SiO$_2$ | | 100 | 300 | 150 | #31 | 26.5 | 5.5 | 37.0 | 23.7 | 7.3 | |
| | | | | | #33 | 26.4 | 6.0 | 36.9 | 23.8 | 6.8 | |
| | | | | | #36 | 26.6 | 5.8 | 37.1 | 24.2 | 6.3 | (b) |

(a) 12-Tungstophosphoric Acid-On-Silica Gel, Sample 6298-6
(b) On-Line-Sample

EXAMPLE 10

This example illustrates the synthesis of methyl t-butyl ether using the equipment and procedures of Examples 1 and 2, but with a 12-tungstophosphoric acid-on-titania catalyst that has 4.1% tungsten loading. The catalyst was prepared by the incipient wetness technique outlined SUPRA. the support is the Norton titania extrudate with a surface area of 51 m$^2$/g.

Product composition data are summarized in Table XI.

TABLE XI

| Catalyst | Feed Sample | Flow Rate (cc/hr) | Pressure (psig) | Temp. (°C.) | Sample | PRODUCT COMPOSITION (WT %) | | | | | |
|---|---|---|---|---|---|---|---|---|---|---|---|
| | | | | | | MTBE | i-C$_4$ | MEOH | tBA | H$_2$O | |
| | F | | | | | | | 46.5 | 53.5 | | |
| H$_3$PO$_4$.12WO$_3$/TiO$_2$(a) | | 25 | 300 | 120 | #1 | 25.0 | 1.8 | 38.4 | 29.0 | 5.9 | |
| | | | | | #3 | 25.5 | 3.1 | 37.3 | 28.1 | 6.1 | |
| | | | | | #6 | 25.5 | 3.2 | 37.3 | 28.1 | 5.9 | (b) |
| " | | 25 | 300 | 150 | #7 | 39.6 | 7.8 | 31.1 | 12.8 | 8.7 | |
| | | | | | #8 | 39.5 | 6.2 | 31.4 | 13.1 | 9.8 | |
| | | | | | #12 | 36.2 | 6.2 | 33.7 | 14.9 | 9.0 | (b) |
| " | | 100 | 300 | 150 | #13 | 27.1 | 5.5 | 37.1 | 22.9 | 7.4 | |
| | | | | | #15 | 26.5 | 5.2 | 37.5 | 23.5 | 7.3 | |
| | | | | | #18 | 26.9 | 7.1 | 36.7 | 22.5 | 6.9 | (b) |

(a) 12-Tungstophosphoric Acid-On-Titania, Sample 5972-86R, W 4.1%
(b) On-Line Sample

EXAMPLE 11

This example illustrates the synthesis of methyl t-butyl ether using the equipment and procedures of Example 1, but with a 12-molybdosilicic acid-on-titania catalyst. This catalyst was prepared by the incipient wetness technique described SUPRA. the support was a Norton titania extrudate with a surface area of 51 m$^2$/g.

Product composition data are summarized in Table XII.

TABLE XII

| Catalyst | Feed Sample | Flow Rate (cc/hr) | Pressure (psig) | Temp. (°C.) | Sample | PRODUCT COMPOSITION (WT %) | | | | | |
|---|---|---|---|---|---|---|---|---|---|---|---|
| | | | | | | MTBE | i-C$_4$ | MeOH | tBA | H$_2$O | |
| | F | | | | | | | 46.0 | 53.8 | | |
| H$_4$SiO$_4$.12MoO$_3$(a) | | 25 | 300 | 120 | #1 | 42.1 | 3.6 | 31.1 | 13.5 | 9.4 | |
| | | | | | #3 | 41.8 | 2.4 | 31.7 | 14.0 | 9.8 | |
| | | | | | #5 | 44.6 | 4.0 | 30.2 | 13.0 | 8.2 | (b) |
| " | | 25 | 300 | 150 | #7 | 40.1 | 3.9 | 32.5 | 13.4 | 9.9 | |
| | | | | | #8 | 38.0 | 5.4 | 33.1 | 11.9 | 10.1 | |

(a) 12-molybdosilicic Acid-On-Titania, Sample 6298-3
(b) On-Line-Sample

EXAMPLE 12

This example illustrates the synthesis of methyl t-butyl ether using the equipment and procedures of Example 1, but with a 12-tungstosilicic acid-on-titania catalyst. This catalyst was prepared by the incipient wetness technique described SUPRA. The support was the titania extrudate from the Norton Company with a surface area 51 m$^2$/g.

Product composition data are summarized in Table XIII; for Sample #4 taken at 120° C.
Estimated TBA Conversion is 76%
MTBE Yield (Basis TBA Converted = 88 mole %

TABLE XIII

| Catalyst | Feed Sample | Flow Rate (cc/hr) | Pressure (psig) | Temp. (°C.) | Sample | PRODUCT COMPOSITION (WT %) | | | | | |
|---|---|---|---|---|---|---|---|---|---|---|---|
| | | | | | | MTBE | i-C$_4$ | MEOH | tBA | H$_2$O | |
| | F | | | | | | | 46.5 | 53.5 | | |
| H$_4$SiO$_4$.12WO$_3$(a) | | 25 | 300 | 120 | #1 | 41.9 | 3.7 | 31.9 | 13.0 | 9.4 | |
| | | | | | #4 | 42.5 | 3.2 | 31.6 | 12.9 | 9.6 | |
| | | | | | #6 | 41.8 | 4.5 | 31.6 | 13.0 | 9.0 | (b) |
| " | | 25 | 300 | 150 | #8 | 36.0 | 7.8 | 34.2 | 10.6 | 10.6 | |
| | | | | | #11 | 36.4 | 7.5 | 34.2 | 10.4 | 10.6 | |
| | | | | | #12 | 35.7 | 9.5 | 33.6 | 10.4 | 10.0 | (b) |
| " | | 150 | 300 | 150 | #13 | 37.9 | 5.6 | 33.7 | 13.0 | 9.7 | |
| | | | | | #17 | 37.7 | 7.1 | 33.4 | 12.1 | 9.7 | |

TABLE XIII-continued

| Catalyst | Feed Sample | Flow Rate (cc/hr) | Pressure (psig) | Temp. (°C.) | Sample | PRODUCT COMPOSITION (WT %) | | | | | |
|---|---|---|---|---|---|---|---|---|---|---|---|
| | | | | | | MTBE | i-C$_4$ | MEOH | tBA | H$_2$O | |
| | | | | | #18 | 37.8 | 8.3 | 33.0 | 12.0 | 9.0 | (b) |

(a)12-Tungstosilicic Acid-On-Titania, Sample 6298-25.1
(b)On-Line Sample

What is claimed is:

1. A one-step method for producing methyl tertiary butyl ether by reacting tertiary butyl alcohol and methanol in the presence of a catalyst wherein said catalyst is a heteropoly acid having the Keggin structure represented by $H_{8-n}[M_2O_{40}]$ where x=P or Si, M=Mo or W and n is an integer which is 4 or 5, at a temperature of 20° C. to 200° C. and a pressure of 0 to 1000 psig.

2. The method of claim 1 wherein the heteropoly acid is supported on an inert support comprising an oxide selected from the group consisting of oxides of titanium, aluminum, silicon and zirconium.

3. The method of claim 1 wherein the heteropoly acid is selected from the group consisting of 12-tungstophosphoric acid, 12-molybdophosphoric acid, 12-tungstosilicic acid and 12-molybdosilicic acid.

4. The method of claim 3 wherein the titanium-containing oxide is titanium dioxide.

5. The method of claim 6 wherein the titanium oxide has a surface area of greater than 10 m$^2$/g.

6. The method of claim 1 wherein the temperature is in the range 100° to 180° C.

7. The method of claim 1 wherein the pressure is in the range of 50 to 500 psig.

8. The method of claim 3 wherein the weight percent concentration of Mo or W in the formulated catalyst is in the range of 0.1 wt % to 30 wt %.

9. The method of claim 4 wherein the heteropoly acid is 12-molybdophosphoric acid and the molybenum content in the formulated catalyst is 1 to 10 wt %.

10. The method of claim 4 wherein the heteropoly acid is 12-tungstophosphoric acid, and the tungsten content in the formulatedcatalyst is 1 to 30 wt %.

11. The method of claim 1 wherein the heteropoly acid is supported on an inert support selected from the group consisting of alumina, silica and titania, as well as mixtures thereof.

12. The catalyst composition of claim 11 wherein the heteropoly acid is 12-tungstophosphoric acid and the inert support is silica.

13. The catalyst composition of claim 11 wherein the heteropoly acid is 12-tungstophosphoric acid and the inert support is alumina.

* * * * *

UNITED STATES PATENT AND TRADEMARK OFFICE
CERTIFICATE OF CORRECTION

PATENT NO. : 4,827,048
DATED : May 2, 1989
INVENTOR(S) : John Frederick Knifton

It is certified that error appears in the above-identified patent and that said Letters Patent is hereby corrected as shown below:

Claim 1, line 14, delete "$[M_2O_{40}]$" and substitute therefor --$[xM_{12}O_{40}]$--.

Claim 10, line 19, delete "formulatedcatalyst" and substitute therefor --formulated catalyst--.

Signed and Sealed this

Twenty-sixth Day of December, 1989

*Attest:*

JEFFREY M. SAMUELS

*Attesting Officer*     *Acting Commissioner of Patents and Trademarks*